United States Patent
Bourque

Patent Number: 5,127,521
Date of Patent: Jul. 7, 1992

[54] TOOTHBRUSH HOLDER UNIT

[76] Inventor: Mark Bourque, P.O. Box 10602, New Iberia, La. 70562-0602

[21] Appl. No.: 748,035

[22] Filed: Aug. 21, 1991

[51] Int. Cl.⁵ ............................................. A61L 2/10
[52] U.S. Cl. .............................. 206/362.1; 206/15.2; 250/455.1; 250/455.11; 422/24
[58] Field of Search .............. 206/15.2, 15.3, 209.1, 206/362, 362.1, 362.2, 362.3; 250/454.1, 455.1; 422/24-26

[56] References Cited

U.S. PATENT DOCUMENTS

| | | | |
|---|---|---|---|
| 1,625,202 | 4/1927 | Gindick | 206/209.1 |
| 1,981,383 | 11/1934 | Feldon | 206/209.1 |
| 2,060,598 | 11/1936 | Tursky | 206/209.1 |
| 2,587,131 | 2/1952 | Ficken | 206/209.1 |
| 2,592,131 | 4/1952 | Farrar | 206/209.1 |
| 3,114,038 | 12/1963 | Meader | 206/209.1 |
| 4,625,119 | 11/1986 | Murdock, III | 250/455.1 |
| 4,906,851 | 3/1990 | Beasley et al. | 250/455.1 |

*Primary Examiner*—Jimmy G. Foster
*Attorney, Agent, or Firm*—Terry M. Gerstein

[57] ABSTRACT

A toothbrush holder unit focuses ultraviolet light onto one or more toothbrushes held in the unit. The brushes are held in separate compartments and can be removed without disturbing other brushes. The ultraviolet light is focused and reflected onto the brushes in such a manner as to ensure that all parts of each brush receive such light and certain areas of each brush will have ultraviolet light concentrated thereon.

14 Claims, 4 Drawing Sheets

FIG. I

TOOTHBRUSH HOLDER UNIT

TECHNICAL FIELD OF THE INVENTION

The present invention relates to the general art of special containers, and to the particular field of toothbrush holders.

BACKGROUND OF THE INVENTION

Many recent studies have concluded that many germs are spread from one person to another via toothbrushes used by such persons. Studies have also concluded that some gum diseases are caused by toothbrushes having certain germs thereon. As simple as this sounds, in hindsight, it makes a great deal of sense since a toothbrush avoids the body's natural defenses by being inserted into a user's mouth. Still further, most toothbrushes are kept in a damp area which is often exposed to a plethora of various germs, especially if someone has a cold.

Therefore, the container art has included several proposals for preventing a toothbrush from being exposed to such germs. These containers work well, but merely preventing exposure to germs is not totally adequate.

Therefore, the art has also included proposals for treating toothbrushes to remove or kill germs. One method which has been proposed includes radiating a stored toothbrush with ultraviolet light. The germicidal properties of ultraviolet light are well documented.

While such designs have worked well, they still have certain drawbacks. For example, the container for the toothbrush may not be amenable to storing a multitude of toothbrushes in a manner which makes those brushes easily accessible while also ensuring that each brush will be fully exposed to the ultraviolet light. Still further, the known containers do not concentrate the ultraviolet light on those areas of the brush that are most likely to be contaminated. In fact, due to the design of many known containers, some parts of a toothbrush may even be shielded from full exposure to the ultraviolet light, and thus a brush may not be fully and adequately radiated by the ultraviolet light.

Therefore, there is a need for a toothbrush storage container which is amenable to storing a plurality of toothbrushes in a manner that makes those brushes easily accessible and which irradiates such stored toothbrushes with ultraviolet light, and focuses that ultraviolet light on all parts of the brush, and concentrates that light on those areas of the brush that are most in need of sterilizing.

OBJECTS OF THE INVENTION

It is a main object of the present invention is to provide a toothbrush storage container which is amenable to storing a plurality of toothbrushes in a manner that makes those brushes easily accessible.

It is another object of the present invention to provide a toothbrush storage container which is amenable to storing a plurality of toothbrushes in a manner that makes those brushes easily accessible and which irradiates such stored toothbrushes with ultraviolet light.

It is another object of the present invention to provide a toothbrush storage container which is amenable to storing a plurality of toothbrushes in a manner that makes those brushes easily accessible and which irradiates such stored toothbrushes with ultraviolet light, and focuses that ultraviolet light on all parts of the brush.

It is another object of the present invention to provide a toothbrush storage container which is amenable to storing a plurality of toothbrushes in a manner that makes those brushes easily accessible and which irradiates such stored toothbrushes with ultraviolet light, and focuses that ultraviolet light on all parts of the brush, and concentrates that light on those areas of the brush that are most in need of sterilizing.

SUMMARY OF THE INVENTION

These, and other, objects are achieved by a toothbrush holder unit which includes a plurality of divider walls and toothbrush holder brackets on a door which can be opened and closed with respect to a housing. An ultraviolet light source is mounted in the housing and directs ultraviolet light towards the holder brackets. The unit also has an ultraviolet light reflecting means in the housing to reflect and redirect the ultraviolet light from the light source onto all parts of the toothbrushes held in the brackets, and in particular against that part of the toothbrushes that, historically, has been found to be most in need of sterilizing.

Specifically, the reflecting means includes a system of mirrors which has a convex mirror mounted on the bottom of the housing to reflect light back in many directions, and two planar mirrors on the dividers to re-reflect such light back towards the toothbrush. The system further includes a concave mirror located adjacent to the toothbrush head having the bristles thereon. Light incident on such concave mirror is focused on the toothbrush near the bristle head.

In this manner, all of the brush is irradiated with ultraviolet light, even those areas that would normally be shaded from the ultraviolet light source either by the holder bracket or by the bristle head, and in fact, the area of the brushes located beneath the holder bracket will have ultraviolet light actually concentrated thereon. It is the area of the brush adjacent to the bristle heads that has been found to be most in need of treatment, and it is this very area that could be shaded from the light source by the bristle head and/or by the holder bracket. It is this area that receives the concentrated ultraviolet light in the unit embodying the present invention.

BRIEF DESCRIPTION OF THE DRAWING FIGURES

DETAILED DESCRIPTION OF THE PREFERRED EMBODIMENT OF THE INVENTION

Figure 1:
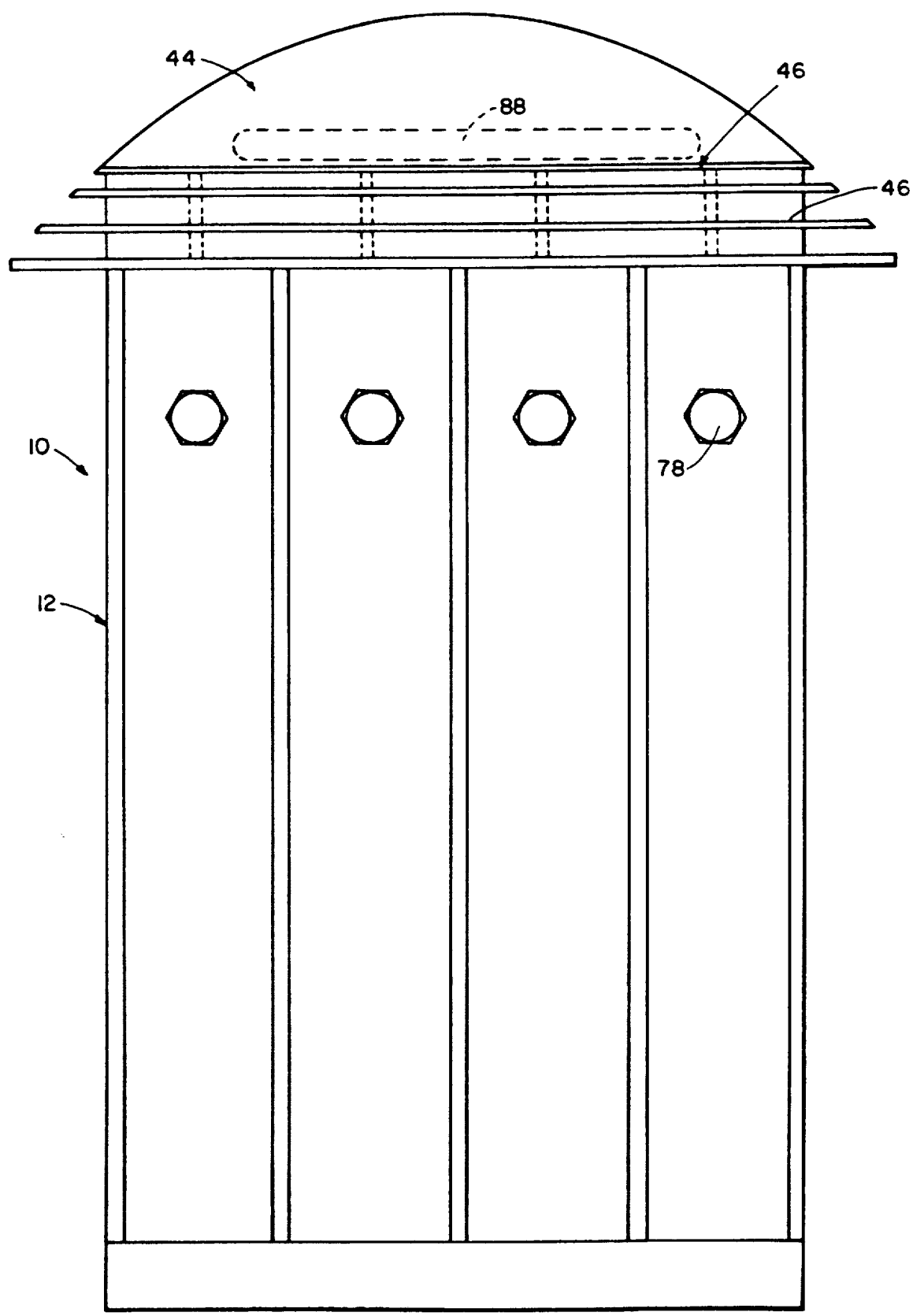
FIG. 1 is a front elevational view of the toothbrush holder unit embodying the present invention.
Figure 2:
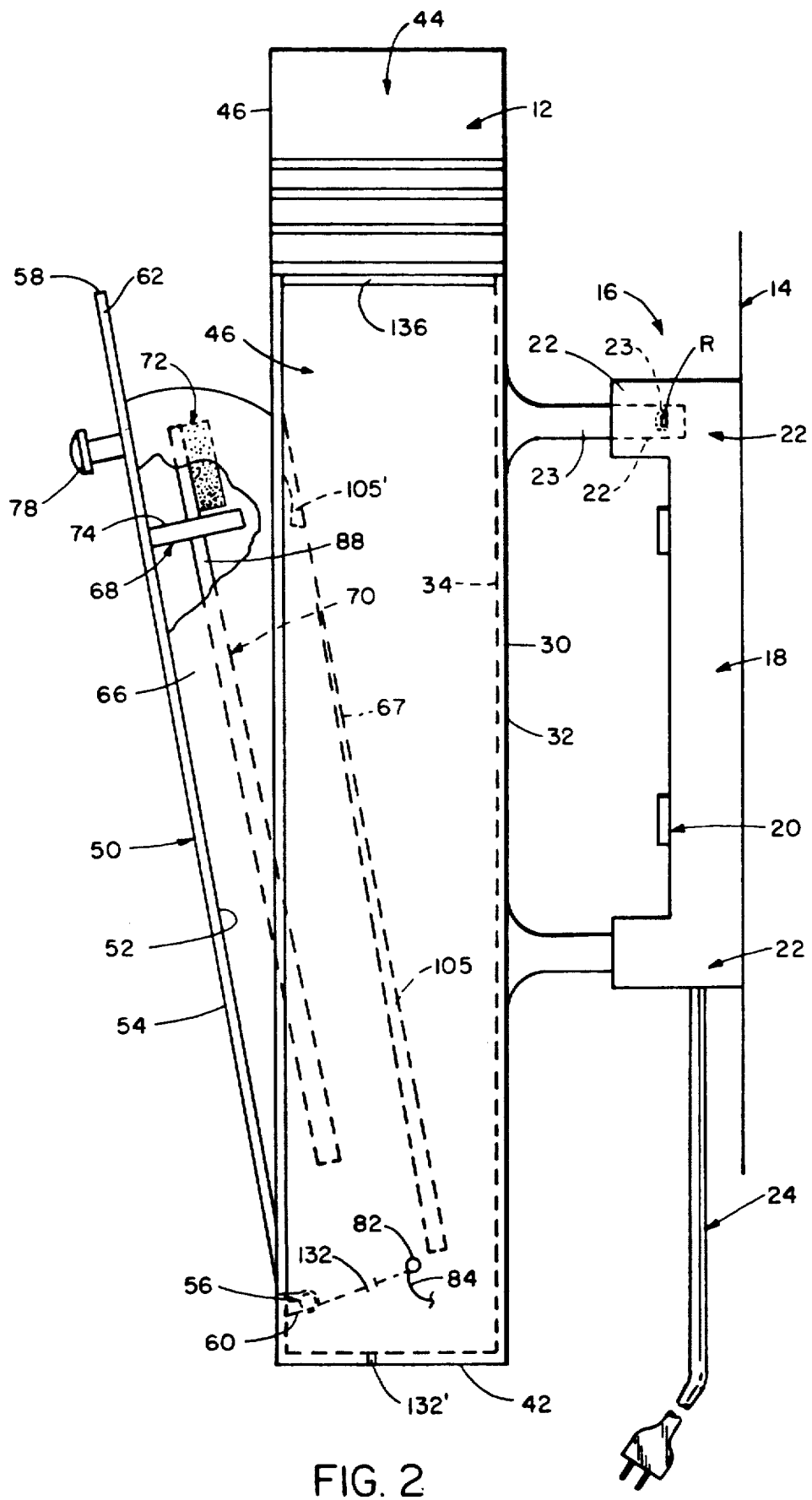
FIG. 2 is a side elevational view thereof.

Shown in FIGS. 1 and 2 is a toothbrush holder unit 10 embodying the present invention. The holder unit 10 includes a hollow housing 12 which is mounted on a support, such as a wall 14, by a mounting assembly 16.

The support assembly 16 includes a base 18 affixed to the wall by screws 20, or like fasteners, and which includes snap-in mounts 22 facing outward from the wall. Electrical wiring 24 is part of an electrical system that brings power, such as utility power, to the holder unit for purposes that will be evident from the ensuing discussion.

The hollow housing 12 includes a rear wall 30 having an outer surface 32 and an inner surface 34, with mounting projections 36 being affixed to the rear wall outer surface 32 and extending outwardly therefrom to be received in the snap-in mounts 22 thereby attaching the hollow housing to the wall.

The housing 12 further includes side walls 38 and 40 attached to the rear wall and extending forwardly therefrom, and a bottom wall 42 attached to the side walls and to the rear wall. It is noted that terms such as "top", "bottom", "side" and the like are taken with respect to the orientation of the housing shown in FIGS. 1 and 2, with the term "outward" being taken in reference to the support wall 14. A top wall 44 is arcuate and dome shaped and connects the top edges of the side walls and the rear wall together, with a front wall 46 extending downwardly from the housing top wall towards the housing bottom wall and being connected to the housing top and side walls. The hollow housing top, side, front and rear walls co-operate to define a cavity 47 inside of the housing.

The housing also includes a door unit 50 having an inner surface 52 and an outer surface 54, and which is pivotally attached to the rest of the housing by a pivot pin 56. The pivot pin 56 is attached to the housing sides and extends thereacross. The door unit is formed by a plurality of individual compartments, and includes a top edge 58 and a bottom edge 60 formed by a plurality of linearly arranged top and bottom edges of the individual compartments, with the sidemost compartments having side edges 62 connecting the top edge to the bottom edge. Each of the individual compartments of the door unit is adapted to assume a closed position with the its top edge located closely subadjacent to the housing front wall 46, and an open configuration shown in FIG. 2, with its side edges at a skewed angle with respect to the housing side walls.

The individual compartments of the door unit are formed by a plurality of divider walls, such as divider wall 66 mounted on the door inner surface to extend from the door bottom edge to near the door top edge. The divider walls are spaced apart along the width dimension of the door as measured between the door side edges. Each individual compartment also includes its own rear wall 67 so that each compartment is open on the top only. Such closed nature of the compartments contributes to the isolation of each toothbrush from other toothbrushes so that germs are not likely to be passed from one brush to another during storage.

Each compartment includes a toothbrush holding mounting bracket, such as mounting bracket 68, affixed to the door unit between adjacent divider walls and extending towards the housing rear wall when the door is closed. A toothbrush 70 is pendently supported on the bracket 68 by the bristle head 72 thereof engaging the top surface 74 of the bracket 68. Each compartment includes a knob 78 on the outside surface thereof and which is grasped to open or close the compartment.

Figure 3:
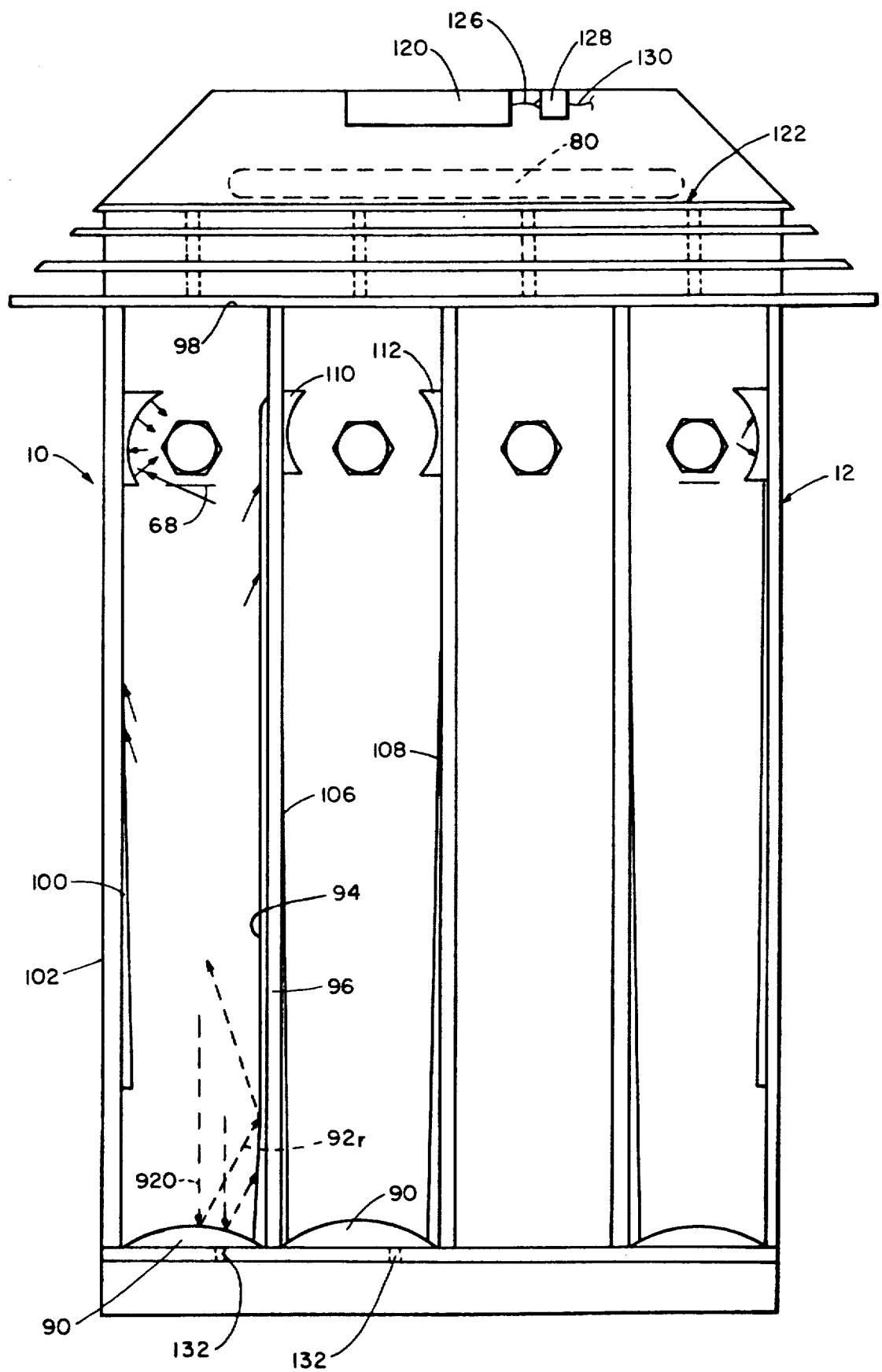
FIG. 3 is front elevational view thereof showing a portion of the ultraviolet light reflecting means included therewith.

As is best shown in FIGS. 1 and 3, an ultraviolet light source 80 is mounted in the housing near the top wall 46 thereof. The light source 80 is connected to the source of power by the cord and by a normally closed switch 82 located adjacent to each compartment and which is depressed to open it and turn the light off when each or any of the compartments is opened. The switches 82 are each connected to the rest of the electrical system by cords, such as cord 84.

The light source 80 directs ultraviolet light into the cavity 47 from above, and some of such light is incident upon the toothbrushes held in each of the compartments.

However, as above discussed, some of the brushes will be shaded from the light by the brackets 68 and/or by the bristle heads 72. Specifically, the neck area 88 of each brush is in the shadow cast by the bracket 68 and the bristle head 72 and will not have light from the source 80 incident thereon. It is this neck area that is most susceptible to germs since it is in contact with the holder and with a user's mouth. Therefore, the neck area should receive special attention with regard to ultraviolet light treatment.

The unit 10 has a special ultraviolet light reflecting system in the housing 12 to reflect ultraviolet from the source 80 onto the toothbrush 70, especially onto the neck area 88 and the bristle area 72 thereof, as that brush is supported on the bracket 68.

The reflecting system in each end compartment includes a convex mirror 90 mounted on the bottom of each compartment to scatter and reflect ultraviolet light that is incident thereon as indicated by rays 92i and 92r in FIG. 3. Only three compartment reflecting systems are shown in FIG. 3; however, it is to be understood that each compartment includes its own reflecting system.

The reflecting system also includes a first planar mirror 94 mounted on divider wall 96 adjacent to the convex mirror 90 and extending from adjacent to that convex mirror to a location spaced above the holder bracket 68 and between that holder bracket and the top edge 98 of the compartment. The mirror 94 is mounted on the divider wall to be angled upwardly as indicated in FIG. 3 so that light incident thereon is reflected in a manner that biases that light upwardly toward the top edge 98.

A second planar mirror 100 is mounted on second divider wall 102 to extend from a location spaced above the convex mirror 90 to a location co-level with the top surface 78 of the holder bracket 68. The second mirror 100 is also slightly angled upwardly to bias light reflected thereby generally upwardly toward the compartment top edge 98. The angles of the first and second mirrors are quite small, in the neighborhood of less than about five degrees.

A convex mirror 104 is mounted on the divider wall 102 adjacent to the holder bracket 68 and extends from the top surface of the holder bracket upwardly toward the compartment top edge 98.

A planar mirror 105 (see FIG. 2, which omits the other mirrors for the sake of clarity of illustration) is also mounted on the rear wall 67 of each compartment. A concave mirror 105' is mounted on the rear wall of the compartment adjacent to the holder 68 to concentrate ultraviolet light onto the bristle head of the toothbrush. Each compartment has such rear mounted planar mirror and rear mounted concave mirror.

All of the mirrors are located with respect to the light source and with respect to each other to reflect, and re-reflect light in a manner that directs that light against each other and, ultimately, against the brush 70, with special concentration of the reflected light occurring on the brush neck area and on the bristle head area.

All of the mirrors in the reflecting system are formed of material that is suitable for reflecting ultraviolet light.

Such materials are disclosed in standard handbooks, such as "Thermal Radiation Properties Survey", by G. G. Gubareff, J. E. Janssen and R. H. Torborg (Minneapolis, MN; Honeywell Research Center, Minneapolis-Honeywell Regulator Company, 1960), the disclosure of which is incorporated herein by reference. Standard textbooks, such as "Engineering Radiation Heat Transfer" by J. A. Weibelt, and published in 1966 by Holt, Rinehart and Winston (the disclosure of which is incorporated herein by reference), also discuss the properties required to efficiently reflect ultraviolet light.

The reflector system in the other end compartment is a mirror image of the just-described reflector system, and thus will not be described in detail.

The midcompartment reflector systems include a convex mirror 90 mounted on the bottom wall of the compartment, and two planar mirrors 106 and 108 extending from adjacent to the convex mirror to approximately co-level with the upper surface of the holder 68. The mirrors 106 and 108 are both angled about five degrees with respect to the divider walls and are angled to face slightly upward towards the compartment upper edge.

The mid-compartments also include two identical concave mirrors 110 and 112 mounted on the divider walls adjacent to and just above the holder top surface, and extend from that top surface toward the compartment top edge. Light from the source or from the planar mirrors or from the convex mirror that is incident on the concave mirrors or on the planar mirrors 106 and 108 will be reflected toward a toothbrush supported on the bracket 68 and toward the other mirrors in the compartment. All of the midcompartment mirror systems are identical, and thus no other such systems will be discussed.

The top wall of the housing as well as the other walls and dividers are opaque to ultraviolet light. Also, referring to FIGS. 1 and 3, the housing includes a vent system which includes a fan 120 which circulates air within the housing cavity 47 and within each compartment to assist in the drying of the toothbrushes stored in the various compartments, and vent holes, such as vent hole 122, fluidically connecting the cavity 47 to the outside. The fan is connected to the power by a cord 126 and a control unit 128 and a further cord 130. The control unit includes a timer circuit that is triggered when any one of the compartments is opened and then closed. Once the compartment is re-closed, the timing circuit in the control unit starts the fan, and lets that fan operate for a preset time in order to circulate enough air to ensure that a toothbrush is dried. Such timing circuits are disclosed in standard textbooks such as "The Encyclopedia of Electronic Circuits" by Rudolf F. Graf, and published in two volumes by TAB Books, Inc in 1988, the pertinent disclosures of which (such as pages 667–671 of volume 2) are incorporated herein by reference.

A weep hole, such as weep hole 132, is located adjacent to each compartment bottom mounted convex mirror so that any moisture in the compartment can be drained from the compartment. The weep hole 132 also serves as part of the air circulation system of the unit so that air from the fan unit can enter the compartment from the open top thereof, circulate through the compartment and then exit that compartment via the hole 132. A companion weep hole 132' is defined in the housing bottom to complete this draining and air circulating function.

Figure 4:
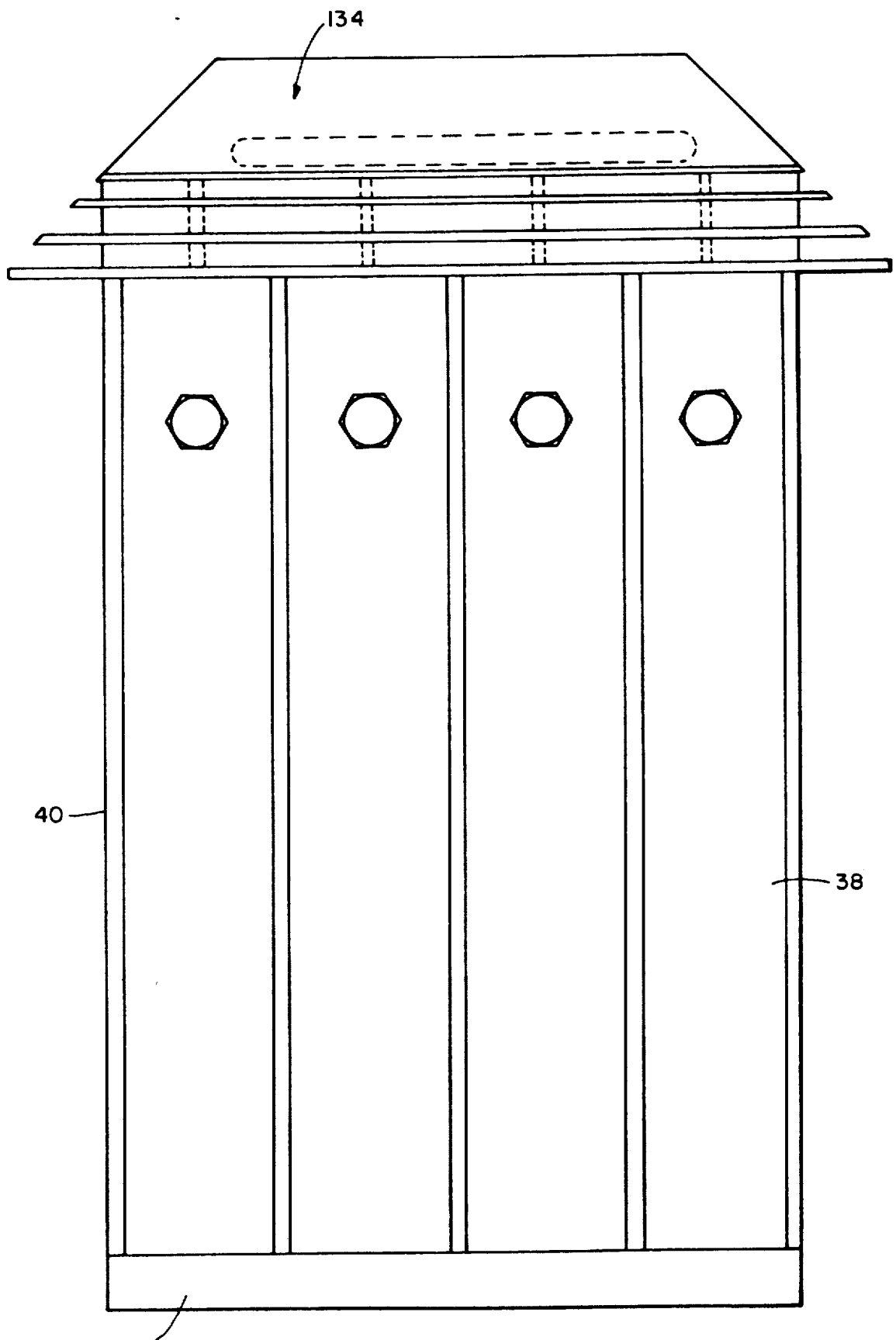
FIG. 4 is a front elevational view of a second form of the toothbrush holder unit embodying the present invention.

An alternative form of the housing is shown in FIG. 4 to include a peaked roof 134. A cover plate 136 can be included to separate the ultraviolet light source from the housing cavity 47 to further ensure the closed nature of the housing. The cover plate 136 has ultraviolet light emitting holes defined therethrough adjacent to each compartment so that light from the source 80 will shine through the plate and into each compartment.

It is also noted that the snap-in elements 22 are formed by a groove 22' on the end of projecting feet 23 affixed to the housing co-operating with a spring-loaded element 23' in the elements 22. A push button release mechanism R moves the springloaded element out of the groove to release the prong from the element 22 so the housing can be removed from the support.

It is understood that while certain forms of the present invention have been illustrated and described herein, it is not to be limited to the specific forms or arrangements of parts described and shown.

I claim:
1. A toothbrush holder unit comprising:
   A) a hollow housing having
      (1) a rear wall,
      (2) a mounting means on said rear wall for mounting said housing on a support,
      (3) side walls connected to said rear wall,
      (4) a top end wall,
      (5) a front wall connected to said top end wall,
      (6) a bottom end wall, and
      (7) a pivot pin connected at each end thereof to said side walls and extending across said housing;
   B) a plurality of compartments attached to said housing, each compartment including,
      (1) a front wall having a top end edge and a bottom end edge,
      (2) a compartment bottom wall connected to said pivot pin;
      (3) two divider walls attached to said compartment front wall,
      (4) a toothbrush holding bracket mounted on said compartment front wall between said divider walls, said holding bracket having a top surface which engages a bristle head of a toothbrush to support such toothbrush in said compartment,
      (5) each of said compartments being pivotable from a closed condition with said compartment front wall top end edge located adjacent to said housing top wall, to an open condition in which said compartment divider walls are at a skewed angle with respect to said housing side walls, and
      (6) said compartment front walls and said housing front wall, said housing side and rear walls all cooperating with each other to define a cavity in which toothbrushes are stored;
   C) an ultraviolet light source mounted on said housing adjacent to said housing top end wall to direct ultraviolet light into said cavity and between said divider walls;
   D) electrical connection means for connecting said ultraviolet light source to a source of power; and
   E) ultraviolet light reflecting means in said compartments to reflect ultraviolet light onto toothbrushes located in said compartments and concentrating ultraviolet light onto neck areas and onto bristle heads of such toothbrushes and including
      (1) a convex mirror mounted on said compartment bottom wall,

(2) a first planar mirror mounted on one of said divider walls and extending from adjacent to said convex mirror to adjacent to said holder bracket, (3) a second planar mirror mounted on a second divider wall and extending from adjacent to said convex mirror to adjacent to said holder bracket, and (4) a concave mirror mounted on said first divider wall adjacent to said holder bracket and located to concentrate ultraviolet light incident thereon on a toothbrush held in said holder bracket.

2. The toothbrush holder unit defined in claim 1 wherein said planar mirrors are both angled with respect to said divider walls at a skewed angle.

3. The toothbrush holder unit defined in claim 2 wherein said skewed angle is about five degrees.

4. The toothbrush holder unit defined in claim 3 further including a second concave mirror on said second divider wall and located adjacent to said holder bracket.

5. The toothbrush holder unit defined in claim 3 wherein said first planar mirror extends to a location between said holder bracket and said compartment front wall top end edge.

6. The toothbrush holder unit defined in claim 5 wherein said concave mirror extends from adjacent to said holder bracket to a location spaced between said holder bracket and said compartment front wall top end edge.

7. The toothbrush holder unit defined in claim 6 wherein said housing top end wall is dome shaped.

8. The toothbrush holder unit defined in claim 6 further including a knob on the front wall of each compartment.

9. The toothbrush holder unit defined in claim 8 further including a vent system in said housing.

10. The toothbrush holder unit defined in claim 9 wherein said vent system includes a fan and a control circuit.

11. The toothbrush holder unit defined in claim 10 wherein said vent system includes vent holes defined in said housing.

12. The toothbrush holder unit defined in claim 11 further including a weep hole system defined in said housing.

13. The toothbrush holder unit defined in claim 12 wherein said electrical connection means includes a normally closed switch which is opened when any of said compartments is opened to turn off said ultraviolet light.

14. The toothbrush holder unit defined in claim 13 wherein said housing mounting means includes a snap-in mount.

* * * * *